United States Patent
Fattinger et al.

(10) Patent No.: US 7,857,575 B2
(45) Date of Patent: Dec. 28, 2010

(54) STACKER

(75) Inventors: Christoph Fattinger, Blauen (CH); Thomas Zumstein, Weil am Rhein (DE); Remo Anton Hochstrasser, Oberwil (CH); Dieter Voegelin, Sissach (CH)

(73) Assignee: F. Hoffmann-LaRoche AG, Basel (CH)

( * ) Notice: Subject to any disclaimer, the term of this patent is extended or adjusted under 35 U.S.C. 154(b) by 336 days.

(21) Appl. No.: 12/079,756

(22) Filed: Mar. 27, 2008

(65) Prior Publication Data

US 2008/0260511 A1 Oct. 23, 2008

(30) Foreign Application Priority Data

Mar. 29, 2007 (EP) .................... 07105217

(51) Int. Cl.
*B65G 59/06* (2006.01)
*B65G 59/00* (2006.01)
*B65H 3/30* (2006.01)
*G07F 11/16* (2006.01)

(52) U.S. Cl. ................. 414/798.1; 414/797.4; 221/293; 221/297

(58) Field of Classification Search ................ 221/154, 221/221–224, 232, 238, 245–246, 267, 289, 221/295, 297, 299, 301, 307; 414/226.02, 414/794.9, 795.3, 795.6, 797.4, 797.8–797.9, 414/798–798.1
See application file for complete search history.

(56) References Cited

U.S. PATENT DOCUMENTS 388,369 A * 8/1888 Morse et al. ................. 194/270

(Continued)

FOREIGN PATENT DOCUMENTS

EP 1 155 743 A2 11/2001

(Continued)

OTHER PUBLICATIONS

Society for Biomolecular Screening,. ANSI/SBS Jan. 2004: for Microplates—Footprint Dimensions, http://www.sbsonline.org: Society for Biomolecular Screening, 2004.

(Continued)

*Primary Examiner*—Gregory W Adams
(74) *Attorney, Agent, or Firm*—Mintz, Levin, Cohn, Ferris, Glovsky & Popeo P.C.

(57) ABSTRACT

A stacker (1) for storing a plurality of microplates each having a top surface side and a bottom surface side opposed to the top surface side, comprises a housing and a removal gate (13) for removing a microplate of the plurality of microplates out of the housing. The stacker (1) is arranged to accommodate the plurality of microplates inside the housing such that the top surface side of one microplate of the plurality of microplates abuts on the bottom surface side of an adjacent microplate of the plurality of microplates and such that the housing adjoins to the plurality of microplates. Using such a stacker 1, the plurality of microplates can be arranged and stored in a compact manner wherein the single microplates of the plurality of microplates can still selectively and efficiently be accessed. Further, due to the controlled access to the plurality of microplates being arranged inside the housing of the described stacker 1 via the removal gate 13, icing of the microplates can be minimized when the stacker is cooled for long term storage of samples arranged inside the microplates.

18 Claims, 8 Drawing Sheets

U.S. PATENT DOCUMENTS

| | | | | | |
|---|---|---|---|---|---|
| 1,126,194 | A | * | 1/1915 | Graham | 414/798 |
| 1,750,391 | A | * | 3/1930 | Coyle et al. | 414/797.8 |
| 3,517,482 | A | * | 6/1970 | Beninger | 53/387.2 |
| 5,092,734 | A | * | 3/1992 | Sakoda et al. | 414/798 |
| 5,415,519 | A | * | 5/1995 | Lee et al. | 414/795.3 |
| 5,674,047 | A | * | 10/1997 | Lapeus et al. | 414/795.6 |
| 5,876,180 | A | * | 3/1999 | Sims | 414/795.6 |
| 6,688,123 | B2 | | 2/2004 | Felder et al. | |
| 6,979,425 | B1 | | 12/2005 | Ganz et al. | |
| 2002/0176803 | A1 | * | 11/2002 | Hamel et al. | 422/100 |
| 2004/0152188 | A1 | | 8/2004 | Yamamoto et al. | |

FOREIGN PATENT DOCUMENTS

| | | |
|---|---|---|
| EP | 0 904 841 B1 | 1/2004 |
| WO | WO 2005/085874 A1 | 9/2005 |

OTHER PUBLICATIONS

Society for Biomolecular Screening, ANSI/SBS Feb. 2004: for Microplates—Height Dimensions, http://www.sbsonline.org: Society for Biomolecular Screening, 2004.

Society for Biomolecular Screening, ANSI/SBS Mar. 2004: for Microplates—Bottom Outside Flange Dimensions, http://www.sbsonline.org: Society for Biomolecular Screening, 2004.

Society for Biomolecular Screening, ANSI/SBS Apr. 2004: for Microplates—Well Positions. http://www.sbsonline.org: Society for Biomolecular Screening, 2004.

GenVault Desktop Archive, www.genvault.com, 2005 GenVault Corporation (1 pg.).

REMP Automated Sample Stores, Small-Size Store (SSS), REMP Sample Management, 2005 by REMP, AG, 04/06 (2 pgs.).

REMP Tube Punching Module,, REMP Sample Management, 2005 by REMP, AG, 06/06 (2 pgs.).

REMP Sample Storage Systems, REMP Storage Family, REMP Sample Management, 2005 by REMP, AG, 08/06 (6 pgs.).

Dr. John Comley, "Automated BioBanking", Drug Delivery World Summer 2007, (8 pgs.).

European Search Report for Application No. EP 07105217.9 dated Sep. 28, 2007.

* cited by examiner

STACKER

This application claims priority to European Patent Application No. 07105217.9, filed Mar. 29, 2007. The contents of this priority application are incorporated by reference into this specification in its entirety.

TECHNICAL FIELD

The present invention relates to a stacker for storing a plurality of microplates according to the preamble of independent claim 1 in general and more particular to a storage unit comprising a plurality of stackers, a freezer box for a stacker or a storage unit, a microplate handling system with a freezer box, a cold room for a microplate handling system, and a microplate handling method using a microplate handling system.

BACKGROUND ART

In chemical, biochemical, biological and pharmaceutical fundamental and applied research automated high-throughput assays are frequently applied to gain knowledge about chemical compounds, biological samples, clinical samples and processes related to the assayed compounds and samples. For example, in drug discovery processes, a wide variety of high-throughput experiments can be carried out to explore the biological activity of molecules. Particularly, in cases where there exists only little knowledge about the structure-activity relation between a biological target and compounds interacting with the target, high-throughput screening (HTS) is typically applied.

Usually in HTS-experiments large numbers of compound samples are assayed wherein the samples are frequently used in small amounts, for example in the range of few microliters, and handled in microplates. Widespread standards defining microplates of about 127.76 mm length, 85.48 mm width and various heights comprising 96, 384 or 1536 wells have been developed by the Society for Biomolecular Sciences (SBS) and have been approved by the American National Standards Institute (ANSI) [see Society for Biomolecular Sciences. ANSI/SBS 1-2004: Microplates—Footprint Dimensions, ANSI/SBS 2-2004: Microplates—Height Dimensions, ANSI/SBS 3-2004: Microplates—Bottom Outside Flange Dimensions and ANSI/SBS 4-2004: Microplates—Well Positions. http://www.sbsonline.org: Society for Biomolecular Sciences, 2004.]. Using such microplates, each sample is held in a fixed and well-defined position in the plate such that automated handling of the samples is possible. As an alternative to microplates having wells for accommodating the samples, standard compliant microplates having removable microtubes instead of wells are also used. Such microtubes can be advantageous since they can be sealed and thereby easily transferred between several microplates in a sealed state. Particularly, when the samples additionally are held frozen inside the microtubes, they can efficiently be transferred from one microplate to another microplate without impairing the frozen state of the samples.

For having compound samples ready when needed for an HTS-experiment specific libraries are set up wherein large numbers of samples, i.e. millions of compound samples, can be stored in accordingly large amounts of microplates. Typically, the microplates comprising the compounds are thereby cooled, for example to −20° C., for ensuring long term stability and stored in a humidity controlled room. The microplates can be positioned in racks with drawers wherein each drawer, each microplate as well as each well or microtube can be encoded. The compounds needed can be gathered automatically by a robot being as well arranged inside the cooled, humidity controlled room. For example, when using microplates with microtubes, the robot can be moved to a predefined drawer, open the drawer and access a source microplate holding the microtube with a selected compound sample. Then, the robot removes the microtube from the source microplate and inserts it into a delivery microplate. This step can for example be efficiently performed by pushing the microtube through the source microplate into the delivery microplate. Similarly, the robot gathers the next selected compound for the same HTS-experiment of its corresponding source microplate and puts it into the same delivery microplate. At the end the robot provides a set of delivery microplates holding the compounds selected for a certain HTS-experiment. Since typically a number of compounds with specific properties are needed in HTS-experiments, the robot can efficiently gather selected compounds when all compounds are logically ordered in sample libraries with racks as described above.

Such a sample library having racks with drawers and a gathering robot, both being arranged in a humidity controlled room cooled to for example −20° C., is for example described in EP 0 904 841 B1 wherein single microtubes held in a source microplate are pushed into a delivery microplate in a separate transfer station, such that the source microplate has to be relocated to the transfer station and back to the drawer.

High-throughput assays as described above are as well used for clinical studies, wherein samples comprising for example blood and serum are used instead of compounds. Said samples can as well be handled in microplates and reasonably, libraries with such samples are set up as well. For the long term storage of such samples it is not sufficient to cool the samples down to a temperature range as described above but they need to be cooled down to a lower temperature range, as for example to a temperature of about −80° C. However, cooling of a complete humidity controlled room for storing microplates holding the samples as described above to said temperatures is not economically feasible. Further, at said temperatures, standard handling devices, such as for example robots, usually do not work properly. Therefore, particularly for long term storage of microplates, special boxes are known in the art. By using such boxes and thereby reducing the space needed to be cooled down to said temperatures a comparably economic storage of microplates is possible.

For example, such a box is shown in U.S. Pat. No. 6,688, 123, wherein a carousel having vertical racks and an interchange mechanism are arranged in the interior of the box. The microplates are arranged on the vertical racks such that the interchange mechanism is capable of shoving an interchange tray underneath the microplate and thereby removing the microplate from the rack. Since the interchange tray has to be shoved underneath the microplate, the microplates have to be spaced apart from each other. Additionally, the interchange mechanism has to be arranged inside the box as well. Thus, the interior space of the box having to be cooled is comparably large. Further, the interchange mechanism has to be arranged to work at the mentioned temperature ranges which can reduce its configuration possibilities. Still further, the prevention of icing while handling a microplate is a difficult task which can reduce the handling efficiency or which can even impair the samples stored in the microplate.

Therefore there is a need for a device allowing a compact efficient economic storage of microplates and the samples therein as well as for a device and a method allowing an efficient economic handling of microplates and the samples therein.

DISCLOSURE OF THE INVENTION

According to the invention this need is settled by a stacker as it is defined by the features of independent claim 1, by a storage unit as it is defined by the features of independent claim 6, by a freezer box as it is defined by the features of independent claim 11, by a microplate handling system as it is defined by the features of independent claim 13, by a cold room as it is defined by the features of independent claim 21 and by a microplate handling method as it is defined by the features of independent claim 22. Preferred embodiments are subject of the dependent claims.

In particular, the invention deals with a stacker for storing a plurality of microplates each having a top surface side and a bottom surface side opposed to the top surface side. It comprises a housing and a removal gate for removing a microplate of the plurality of microplates out of the housing. The stacker is arranged to accommodate the plurality of microplates inside the housing such that the top surface side of one microplate of the plurality of microplates abuts on the bottom surface side of an adjacent microplate of the plurality of microplates and such that the housing adjoins to the plurality of microplates. Using a stacker as described, the plurality of microplates can be arranged and stored in a compact manner wherein the single microplates of the plurality of microplates can still selectively and efficiently be accessed. Further, due to the controlled access to the plurality of microplates being arranged inside the housing of the described stacker via the removal gate, icing of the microplates can be minimized. Reasonably, the amount of microplates being arrangeable inside the stacker is restricted to a set of for example about five to about hundred microplates, particularly to a set of ten to fifty microplates.

Preferably the housing comprises four essentially perpendicularly arranged walls, wherein each of the walls adjoins each microplate of the plurality of microplates when the housing accommodates the plurality of microplates. Particularly, when standardized microplates of a rectangular base area and therefore having also a rectangular bottom surface side and a rectangular top surface side are used, such perpendicularly arranged walls allow a tight and sealed and compact arrangement of the plurality of microplates in the housing. Additionally, the microplates can exactly be guided while being loaded into the housing and while being removed out of the housing. Further, due to this compact and sealed arrangement of the plurality of microplates being arranged inside the housing of the described stacker, icing of the microplates can be minimized while microplates are loaded to or removed from the stacker and while microplates are stored in the stacker. The walls of the housing can be made of any suitable material and particularly of a suitable plastic material which allows building of a robust housing at comparably low production costs. Particularly, the housing can be made by a molding process which allows an efficient flexible building of the housing at comparably low production costs. In a preferred embodiment, the walls of the housing are made of a transparent material allowing the visual control of the filling status of the stacker as well as allowing automated scanning of codes being attached to the microplates through the walls.

Preferably, each of the walls has a contoured section adjoining each microplate of the plurality of microplates. Like this, it is possible to provide well defined small spacings between the plurality of microplates, i.e. the stack of microplates, and the walls of wider spacings in between for preventing unintentional wedging of the microplates inside the housing of the stacker. Thereby, the housing is arranged to allow an exact guiding of the microplates while being loaded into the stacker and while being removed out of the stacker and to allow a sealed storage of the microplates being arranged inside the housing.

The removal gate preferably is arranged at an open longitudinal end of the housing and preferably has holding means for holding the plurality of microplates inside the housing, such that the holding means project above a border of the open longitudinal end towards the interior of the housing when the stacker is in a closed state. Like this, microplates being arranged inside the housing are held inside the housing by the holding means when the stacker is in a closed state. To remove a microplate being arranged inside the housing out of the housing, the stacker can for example be brought into an open state by moving the holding means such that they do no longer project above the open longitudinal end of the housing towards its interior. Particularly, the removal gate can be arranged at an open longitudinal end at the bottom of the stacker such that a microplate being arranged inside the housing can be removed out of the housing gravitation when the stacker is in the open state. Further, a cover for protecting the interior of the housing can be arranged on the second open longitudinal end of the stacker at which no removal gate is arranged.

In a preferred embodiment, the holding means are resiliently arranged such that they are relaxed when the stacker is in the closed state and such that they are tensioned when the stacker is in the open state. Like this, a comparably simple arrangement is possible that ensures the stacker is in its closed state when no external force acts on the removal gate such that a microplate being arranged in the stacker can not unintentionally be removed from the stacker. The holding means can comprise an angled, flat spring like sheet, for example made of metal, having a mounting portion and a retention portion arranged angled thereto. The end of the mounting portion being away from the retention portion can be mounted to a section of a corresponding wall near the open longitudinal opening such that the retention portion projects towards the inside of the housing. For opening the removal gate, the angled, flat spring like sheet can be bent such that the retention portion no longer projects towards the interior of the housing. Preferably, such an angled, flat spring like sheet is arranged at two opposed walls of the housing. Further, the retention portion preferably is arranged at an acute angle in relation to the mounting portion. Thereby, the retention portion not only projects towards the interior of the housing but also inside the interior of the housing.

Preferably, the stacker comprises a handle for carrying the stacker allowing a comparably easy manual handling of the stacker.

A second aspect of the invention deals with a storage unit comprising a plurality of fixedly interconnected stackers as described above, wherein each of the stackers adjoins to its adjacent stacker. Such a storage unit allows compact storage and efficient handling of a plurality of stackers. Particularly, it also allows an efficient parallel handling of several microplates being stored in several stackers of the plurality of stackers of the storage unit. For example, a complete set of microplates can be removed out of the storage unit in one single step by accessing all the microplates being located closest to the removal gates of each stacker at once. Reasonably, the amount of stackers being comprised by the storage unit is restricted to a set of about three to about ten stackers, particularly to a set of six to eight stackers.

In a preferred embodiment, the stackers are arranged in a row. Such a storage unit can be advantageous for automated handling and for storing. In particular, when the single stackers of the storage unit have a rectangular base area as described above, the stackers are preferably interconnected at their wider sides.

Preferably, the storage unit further comprises a bottom plate being connected to a bottom end of each of the stackers. Such a bottom plate additionally improves the handling-ability of the storage unit, beyond others, for example the stability of the storage unit.

The bottom plate preferably comprises removal openings for removing microplates out of the storage unit, each being arranged adjacent to the removal gate of one of the stackers. Like this, microplates of the plurality of microplates being arranged in the storage unit can be removed out of the storage unit or can be loaded into the storage unit via the openings of the bottom plate without having to remove the bottom plate from the storage unit. Accordingly, the openings can be shaped corresponding to the shape of the base area of the microplates.

In a preferred embodiment, the storage unit further comprises lifting means. Lifting means additionally improve the handling-ability of the storage unit and more particularly they allow a convenient lifting of the storage unit out of and a convenient dropping of the storage unit into a further device, such as for example a freezer box as described below. The lifting means can comprise two bars each having an arrow head and each being arranged at a lateral end of the storage unit. Such lifting means with arrow heads allow to be hooked into a lifting device, such as for example a gantry robot, such that the storage unit can conveniently be handled in an automated manner by the lifting device.

A third aspect of the invention deals with a freezer box for tempering a stacker as described above, or for tempering a storage unit as described above. The freezer box has a temperable interior which is arranged for accommodating the stacker or the storage unit, and an opening at a top side or front side of the freezer box for receiving and removing the stacker or the storage unit into and out of the interior of the freezer box. With such a freezer box allowing the arrangement of a stacker or a storage unit, samples being arranged inside of microplates which again are arranged inside the stacker or the storage unit, respectively, can be stored long term at low temperature in a economic manner since only the interior of the freezer box has to be cooled to a low temperature. In particular, when cooling at a temperature of less than −20° C. and more particular to a temperature of about −80° C. or less is needed, the freezer box allows comparably little space having to be cooled for a sufficient cooling for long term storage of the samples inside the stacker and the storage unit such that efficient economic cooling of the samples is possible. Further, due to the higher density of the cooled air in the interior of the freezer box in relation to the warmer air outside of the freezer box, there is only minimum convective heat exchange between the interior of the freezer box and the outside of the freezer box via the opening at the top side of the freezer box even when the opening is not covered. Therefore, the opening doesn't need to be covered for preventing a warming of the samples being inside the stacker or the storage unit in the interior of the freezer box such that at least the loading and the retrieval of the stacker or the storage unit, respectively, may be easily performed. The space inside the freezer box can be scaled to the needs of the application of the freezer box by serially arranging several freezer boxes, for example in a row.

Preferably, the freezer box has a cuboid shape and a plurality of shafts, wherein each shaft has its open end at the top side of the freezer box and each shaft is arranged for accommodating a stacker or a storage unit. Such a freezer box allows a further improved tempering of a plurality of stackers or storage units, respectively. It keeps the all over space needed to be tempered on a small level allowing an efficient and economic tempering of the plurality of stackers or of storage units, respectively.

A fourth aspect of the invention deals with a microplate handling system comprising a freezer box as described above, a plate tray, a positioning disposition and a robot arm. The plate tray and the positioning disposition are arranged to accommodate at least one source microplate with a plurality of microtubes and a delivery microplate such that a top surface side of the delivery microplate is arrangeable facing a bottom surface side of the at least one source microplate. The positioning disposition has moving means for moving the at least one source microplate and the delivery microplate parallel in relation to each other into a predefined position when the plate tray and the positioning disposition accommodate the at least one source microplate and the delivery microplate. The robot arm has pushing means for pushing a predefined microtube of the plurality of microtubes from the at least one source microplate into the delivery microplate when the plate tray and the positioning disposition accommodate the at least one source microplate and the delivery microplate and when the at least one source microplate and the delivery microplate are moved to the predefined position by the moving means.

Such a microplate handling system allows an efficient and fast handling of microplates being stored in stackers or in storage units which are stored in the freezer box. Particularly, if a plurality of predefined samples being contained in predefined microtubes inside the stacker or the storage unit which is stored in the freezer box have to be picked, for example for performing a specific high-throughput assay, the microplate handling system allows to provide at least one delivery plate carrying the microtubes with the predefined samples. Typically, the delivery microplate is arranged according to general microplate standards as described above and can accommodate microtubes into corresponding receiving means. Preferably, the at least one source microplate and the delivery microplate are of the same type such that one single type of microplates can be used for the whole microplate handling system.

The positioning disposition and the plate tray of the microplate handling system allow to position the at least one source microplate and the delivery microplate very exactly in relation to each other such that the robot arm can precisely push predefined microtubes from the at least one source microplate into the delivery microplate. Suitable robot arms which are comparably fast, precise and cost efficient are known in the art, for example as Selective Compliant Articulated/Assembly Robot Arm (SCARA), wherein according to the invention such a SCARA is additionally provided with pushing means. As it can be seen by a person skilled in the art, the robot arm of the invention can also be used in other microplate handling systems known in the art such as for example in the system of EP 0 904 841 B1 as described above. Further, the robot arm can have a sensor, such as for example a camera, for sensing the precise position of the at least one source microplate. Suitable pushing means can comprise a pin being used to transfer a predefined microtube of the at least one source microplate into the delivery plate. In one embodiment, such a pin can be moved into the direction of the single microtube by a pushing mechanism independently of the other parts of the robot arm such that the pin can be moved in relation to the rest of the robot arm. In another embodiment, the pin is fixedly connected with the rest of the robot arm and is moved into the direction of the predefined microtube by the movement of the robot arm itself.

In a preferred embodiment the plate tray is arranged for fixedly accommodating the at least one source microplate in a predefined position and the positioning disposition is arranged for movably accommodating the delivery microplate. The moving means of the positioning disposition are arranged for moving the delivery microplate with its top surface side parallel to the bottom surface side of the at least one source microplate into the predefined position when the positioning disposition accommodates the delivery microplate and the plate tray accommodates the at least one source microplate. Such an arrangement of the plate tray and the positioning disposition is comparably efficient since the number of movable parts can be reduced and since it is comparably simple to provide sufficient precision when the at least one source microplate is fixedly accommodated. Further, the microtubes of the at least one source microplate can comparably easily been pushed from the source microplate into the delivery microplate when the top surface side of the delivery microplate faces the bottom surface side of the at least one source microplate. Still further, with a parallel movement of the delivery microplate in relation to the at least one source microplate it is sufficient for the positioning disposition to be capable of moving the delivery microplate in two dimensions. This allows a comparably simple arrangement of the positioning disposition even at the precision scale of movement needed.

Preferably, the plate tray has at least one through-hole adjoining the bottom surface side of the at least one source microplate when the plate tray accommodates the at least one source microplate. Such a plate tray allows a comfortable pushing of microtubes from the at least one source microplate into the delivery microplate via the at least one through-hole while the at least one source microplate can be held in a precisely predefined position. For example, the border of the through-hole can be arranged as a step with a tread and a riser wherein the riser adjoins essentially perpendicularly to the top side of the plate tray and the tread adjoins essentially perpendicularly to the riser. In use a microplate can be laid in the opening such that the tread in the at least one through-hole contacts a border section of the bottom surface side of the microplate and such that the riser fixes the microplate in an exactly predefined position.

In a preferred embodiment the microplate handling system further comprises a platform, particularly a robotic platform, being arranged on top of the freezer box, and a gantry robot being arranged on the platform, wherein the platform has a through hole and the gantry robot has gripping means for gripping the stacker or the storage unit such that the stacker or the storage unit is liftable through the through hole of the platform out of the freezer box by the gantry robot and such that the stacker or the storage unit can be dropped through the through hole of the platform into the freezer box by the gantry robot. Such an arrangement of a platform and a gantry robot allows an efficient handling of complete stackers or storage units in relation to the freezer box. If a freezer box with a plurality of shafts is used as described above, the platform can accordingly have several openings corresponding to several of the plurality of shafts. The gripping means can be arranged to interact with the lifting means of the storage unit, for example it can be arranged to hook into arrow heads of the lifting means and to release the arrow heads of the lifting means. Further, the freezer box can be connected to rails and the platform can have corresponding moving means such that the platform can be moved along one or several row wise arranged freezer boxes.

Preferably, the microplate handling system further comprises a source microplate handling disposition having removal means for removing the at least one source microplate out of a first stacker or out of a first storage unit when the first stacker or the first storage unit is lifted out of the freezer box, accommodation means for transferring the at least one source microplate to the plate tray and for accommodating the at least one source microplate on the plate tray, as well as putting means for transferring the at least one source microplate from the plate tray to a second stacker or a second storage unit and for putting the at least one source microplate into the second stacker or the second storage unit. In particular, the removal means of the source microplate handling disposition can have releasing means for providing the first stacker or the first storage unit into its open state, for example by bending according holding means, and a plate lift for accommodating a single microplate being removed from the stacker or a single row of microplates being removed from the storage unit. Such an arrangement allows the removal and positioning of a predefined microplate or of a row of predefined microplates before being processed by the robot arm as well as the removal of the predefined microplate or of the row of predefined microplates into the second stacker or the second storage unit after being processed by the robot arm. Typically, all microplates of the first stacker or of the first storage unit are transferred into the second stacker or the second storage unit while being handled, wherein microplates not carrying predefined microtubes can directly been transferred to the second stacker or the second storage unit without being processed by the robot arm.

In a preferred embodiment, the microplate handling system further comprises a delivery microplate handling disposition having an additional stacker as described above, and putting means for transferring the delivery microplate to the additional stacker and for putting the delivery microplate into the additional stacker. Like this, several delivery plates in which microtubes have been gathered can be collected in a single stacker as handling unit.

Preferably, the microplate handling system further comprises an interim storage, wherein the robot arm has gripping means for gripping the delivery microplate, such that the delivery microplate is moveable into the interim storage by the robot arm. Such an interim storage provides a multitude of delivery plates containing independent collections of microtubes. The interim storage can be arranged as a rack which is easy accessible be the gripping means of the robot arm.

In a preferred embodiment the microplate handling system further comprises a tempering cap being tightly connected to the platform, having tempering means and enclosing the plate tray, the positioning disposition, the robot arm, and the gantry robot, such that the interior of the tempering cap is temperable by the tempering means separately from the tempering of the freezer box. Using such a tempering cap allows to handle microplates at a temperature which is different from the temperature optimized for the long term storage of the samples, such as for example $-80°$ C. in the freezer box, and which is different from the temperature outside of the microplate handling system, which for example can be $+4°$ C. or room temperature. Thereby, it is possible to provide a temperature suitable for the operation of mechanical components of the microplate handling system, for example the robot arm, and suitable for not impairing the samples inside the microplate while the microplate is handled. An according temperature can be for example $-20°$ C.

A fifth aspect of the invention deals with a cold room for a microplate handling system as described above comprising at least a first compartment, a second compartment, a third compartment and a dry-air conditioning system. The first compartment being operated at an elevated temperature, for example about +4° C., has a docking port for loading the freezer box of the microplate handling system into the cold room and for de-loading the freezer box of the microplate handling system out of the cold room. The second compartment is operated at a low temperature, for example about –80° C., for storing a stacker as described above or a storage unit as described above and the third compartment is operated at an intermediate temperature, for example about –20° C., suitable for automated microplate handling. The docking ports of the first compartment allow convenient loading of freezer boxes into the cold room and convenient de-loading of freezer boxes out of the cold room. The intermediate temperature can be high enough to avoid mechanical problems due to a very low temperature environment and low enough to keep samples frozen and thereby safeguarding sample quality during automated sample handling. The dry-air conditioning system of the cold room prevents frost built-up during microplate storage and during microplate handling.

A sixth aspect of the invention deals with a microplate handling method using the microplate handling system described above comprising the steps of:

a) tempering the freezer box to a predefined temperature range;
b) storing a plurality of storage units with a plurality of stackers each having a plurality of source microplates with a plurality of microtubes inside the freezer box;
c) providing an empty second storage unit corresponding to the storage unit;
d) accommodating a delivery microplate on the positioning disposition;
e) moving one storage unit of the plurality of storage units out of the freezer box;
f) transferring at least one source microplate via the removal gate of the corresponding at least one stacker to the plate tray;
g) simultaneously positioning the delivery microplate and the robot arm such that a bottom side of a predefined microtube of the at least one source microplate is arranged adjacent to a top surface side of the delivery microplate at predefined receiving means of the delivery microplate and such that the pushing means of the robot arm are arranged adjacent to a top side of the predefined microtube;
h) pushing the predefined microtube from the at least one source microplate into the predefined receiving means of the delivery microplate by means of the robot arm;
i) repeating steps g) and h) until all predefined microtubes of the at least one source microplate are pushed into the delivery microplate;
j) transferring the at least one source microplate into the second storage unit;
k) repeating steps f) through j) until all microplates of the storage unit are located inside the second storage unit; and
l) moving the second storage unit into the freezer box.

Such a method allows to efficiently handling microplates and in particular to efficiently gathering predefined samples stored in stackers or storage units.

BRIEF DESCRIPTION OF THE DRAWINGS

The stacker according to the invention, the storage unit according to the invention, the freezer box according to the invention, the microplate handling system according to the invention, the cold room according to the invention, and the method according to the invention are described in more detail hereinbelow by way of exemplary embodiments and with reference to the attached drawings, wherein.

MODE(S) FOR CARRYING OUT THE INVENTION

In the following description certain terms are used for reasons of convenience and are not to be interpreted as limiting. The terms "right", "left", "bottom", "top", and "upward" refer to directions in the figures. The terminology comprises the explicitly mentioned terms as well as their derivations and terms with a similar meaning.

Figure 1:
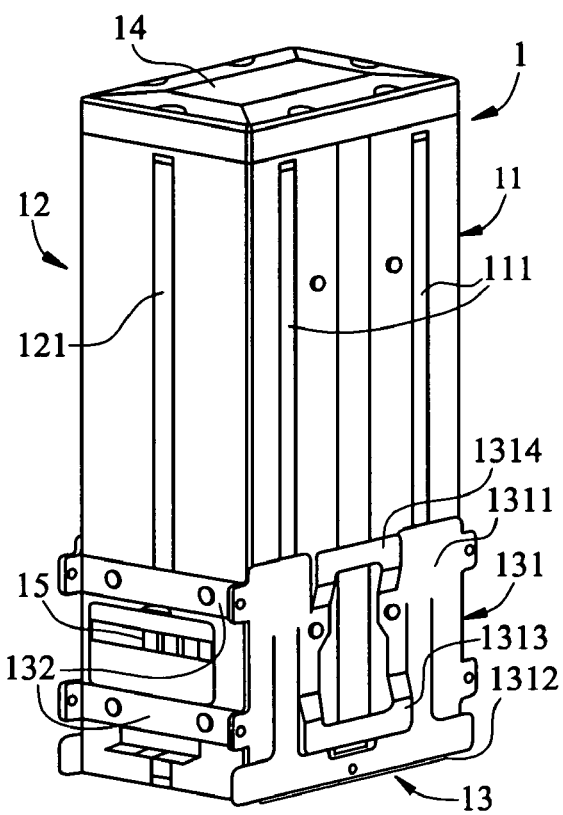
FIG. 1 shows a perspective view on a stacker according to the invention.

In FIG. 1 a stacker 1 according to the invention having a housing with two opposed parallel wider side walls 11 (only one wider side wall 11 is visible in FIG. 1) and two opposed parallel narrower side walls 12 (only one narrower side wall 12 is visible in FIG. 1) which are perpendicularly arranged to the wider side walls 11 is shown. Each of the wider side walls 11 has two parallel contoured sections 111 and each of the narrower side walls 12 has one contoured section 121 wherein all of the contoured sections 111, 112 have the shape of strips slightly extending into the interior of the housing. The housing has two longitudinal open ends wherein the top longitudinal open end is closed by a cover 14 and at the bottom longitudinal open end a removal gate 13 is arranged. The removal gate 13 comprises two angled, flat spring like sheets 131 (only one angled, flat spring like sheet 131 is visible in FIG. 1) each of which being arranged at one of the wider side walls 11. The angled, flat spring like sheet 131 are interconnected by four cross beams 132 (only two cross beams 132 are visible in FIG. 1) wherein two cross beams 132 are parallel arranged at each of the narrower side walls 12. The cross beams 132 are fixed to the angled, flat spring like sheets 131 by means of rivets, screws or the like. Each of the angled, flat spring like sheets 131 comprises a mounting portion 1311 being mounted to one of the wider side walls 11, a retention portion 1312, a bending limiter 1313 sticking out of the angled, flat spring like sheet 131 and a carriage arc 1314. Further, the stacker 1 is coded for identification by a bar code 15 which is attached to one of the narrower side walls 12.

The following applies to the rest of this description. If, in order to clarify the drawings, a figure contains reference signs which are not explained in the directly associated part of the description, then it is referred to previous description parts.

Figure 2:
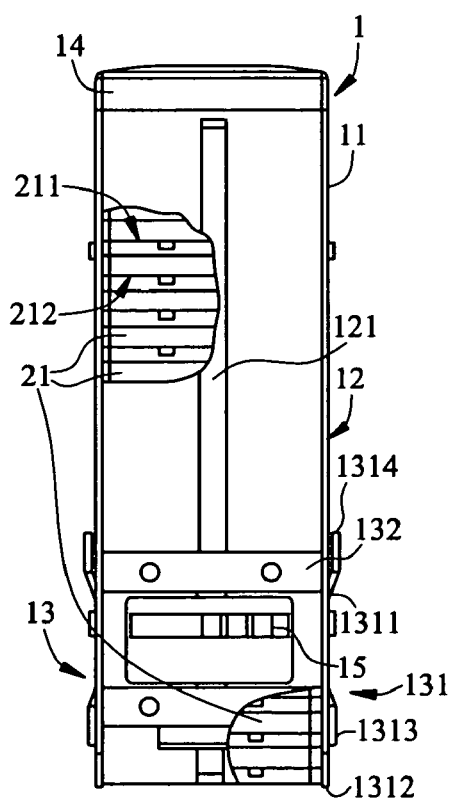
FIG. 2 shows a front view at the stacker from FIG. 1 wherein two sections of the front wall of the stacker are shown schematically opened for making visible the interior of the stacker.

FIG. 2 shows the stacker 1 loaded with a plurality of source microplates 21 each having a top surface side 211 and a bottom surface side 212. The source microplates 21 are arranged inside the housing such that the top side 211 of each of the microplates abuts on the bottom side 212 of its upper adjacent source microplate 21, except for the top source microplate 21 of the plurality of source microplates 21. The contoured sections 111 of the wider side walls 11 and the contoured sections 121 of the narrower side walls 12 adjoin to the plurality of source microplates 21 for exactly guiding them inside the housing. The other sections of the wider side walls 11 and the narrower side walls 12 are arranged slightly apart of the source microplates 21 such that wedging of a source microplate 21 inside the housing can be prevented.

The stacker 1 comprising the source microplates 21 provides a compact robust handling unit for a plurality of source microplates 21 at once such that the source microplates 21 take only little space for storing and such that source microplates 21 are nevertheless convenient to handle, particularly by an automated system. Further, due to the tight arrangement of the source microplates 21 and the housing, icing of the source microplates 21 can be prevented such that it can be exposed to significant temperature changes without risking impairment of substances being arranged in the source microplates 21. Thus, the stacker 1 is an efficient convenient handling unit particularly suitable for storing source microplates 21 at very low temperatures, such as for example at −80° C. It is understood that the stacker 1 can as well be loaded with any other type of microplates than the source microplates 21, such as in particular delivery microplates.

Figure 3:
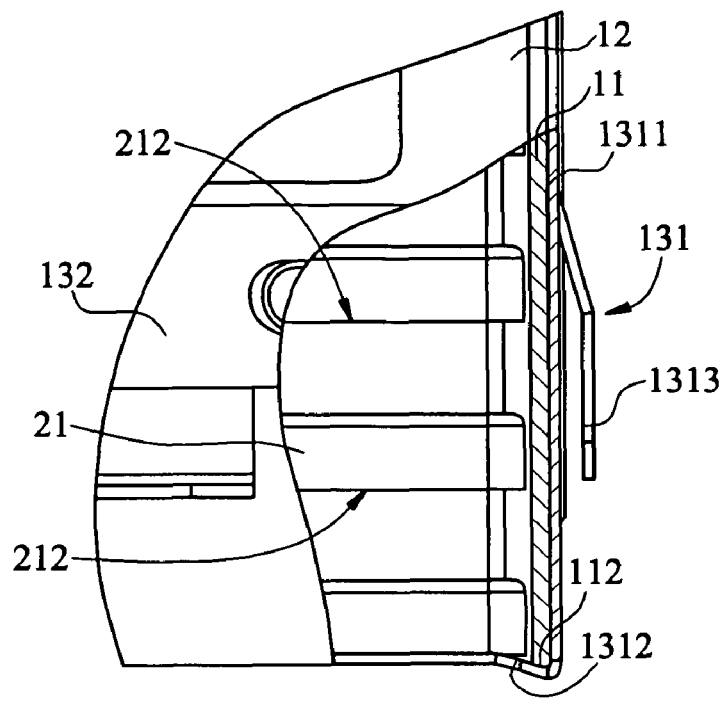
FIG. 3 shows a front view of the right bottom corner section of the stacker from FIG. 1 in a closed state wherein the corner of the front wall is shown schematically opened for making visible the interior of the stacker.

In FIG. 3 the stacker 1 is shown in a closed state. The angled, flat spring like sheet 131 is in a relaxed position wherein the retention portion 1312 projects above a border 112 of the bottom open longitudinal end of the housing towards the interior of the housing thereby covering a part of the bottom longitudinal open end of the housing. The outer border of the bottom source microplate 21 of the plurality of source microplates 21 being arranged in the stacker 1 bears on the retention portion 1312 such that the source microplates 21 are held inside the housing by the retention portion 1312. Further, the retention portion 1312 is arranged in an acute angle in relation to the mounting portion 1311 such that it extends upward further into the interior of the housing.

Figure 4:
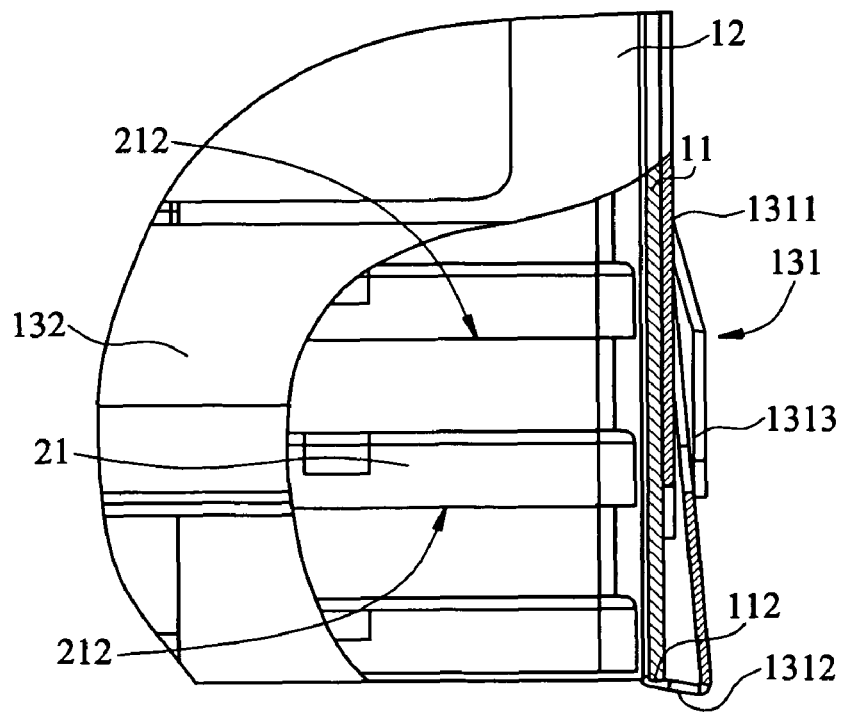
FIG. 4 shows a front view of the right bottom corner section of the stacker from FIG. 1 in an open state wherein the corner of the front wall is shown schematically opened for making visible the interior of the stacker.

FIG. 4 shows the stacker 1 in an open state wherein the retention portion 1312 is bent outward (in FIG. 4 this is the right hand side) the housing such that the bottom open longitudinal end of the housing is free and the source microplates 21 can be removed out of the stacker 1 via the bottom open longitudinal end of the housing. The bending motion of the angled, flat spring like sheet 131 outward the housing is blocked at a certain extent by the bending limiter 1313.

For loading the stacker 1 with an additional source microplate 21, the additional source microplate 21 can be pushed bottom-up against the retention portion 1312 when the stacker 1 is in its closed state. Thereby, the angled, flat spring like sheet 131 is bent outward until it is blocked by the bending limiter 1313. The stacker 1 is then in its open state and the additional source microplate 21 can be pushed into the housing wherein other source microplates 21 already being inside the housing are lifted upwards. For removing a bottom source microplate 21 out of the stacker 1, the retention portion 1312 has to be actively bent outward by appropriate removing means. Such removing means can for example comprise a plate lift which can be pushed bottom-up against the retention portion 1312 and thereby bending the retention portion 1312 outward the housing. The bottom source microplate 21 is then dropped by gravitation onto the plate lift of the removing means. By lowering the plate lift the bottom source microplate 21 is removed from the stacker 1 and simultaneously the retention portion 1312 is moved back by a spring force of the angled, flat spring like sheet 131 until the stacker 1 is again in its closed state.

Figure 5:
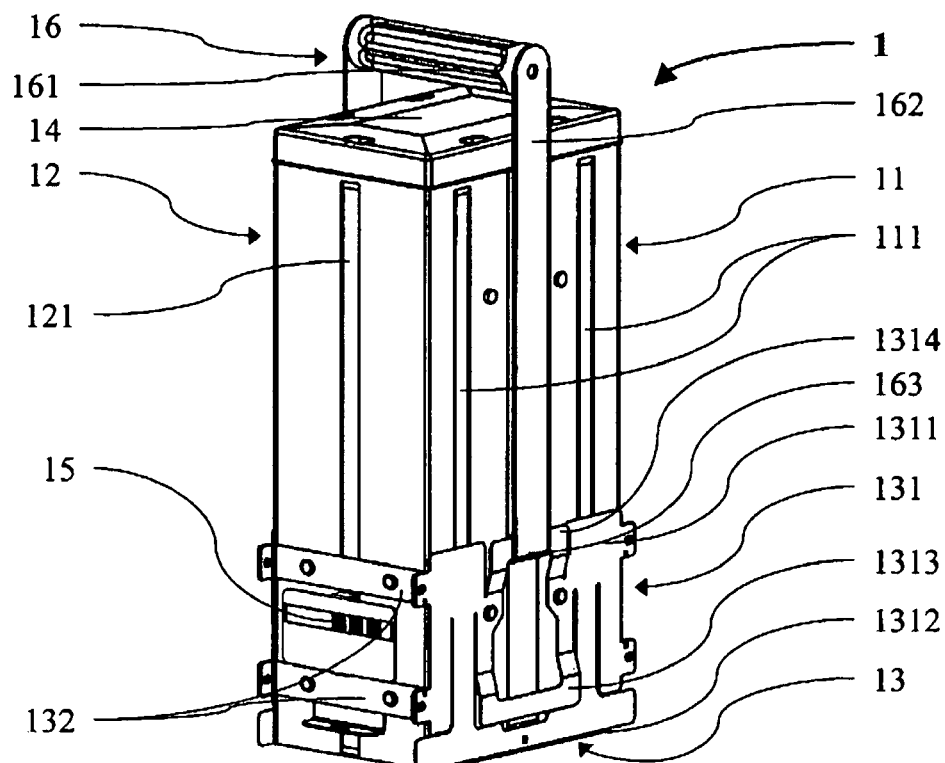
FIG. 5 shows a perspective view on the stacker from FIG. 1 with a removable handle.

As shown in FIG. 5 the stacker 1 can be equipped with a handle 16 having two parallel mounting bars 162 being interconnected at their top longitudinal end by a grip 161. Each of the mounting bars 162 has a hook 163 at its bottom longitudinal end each of them being attachable at one of the carriage arcs 1314 of the removal gate 13. The handle 16 can be connected to the stacker 1 for manual handling of the stacker 1 and can be removed from the stacker 1 such that one single handle 16 can be used for the manual handling of several stackers 1.

Figure 6:
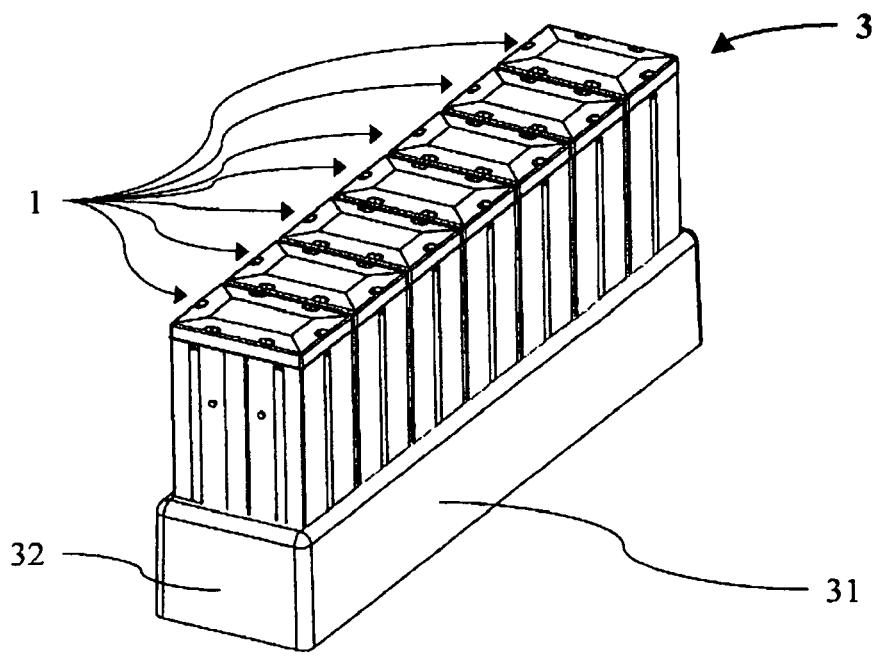
FIG. 6 shows a perspective view of a first embodiment of a storage unit according to the invention.

In FIG. 6 a first embodiment of a storage unit 3 is shown comprising seven stackers 1 which are arranged in a row such that one of the two wider side walls 11 of one stacker 1 faces one of the two wider side walls 11 of its adjacent stacker 1. The storage unit 3 further comprises two parallel wider side plates 31 interconnected by two perpendicularly arranged narrower side plates 32. The side plates 31, 32 together fix the seven stackers 1 in its position to each other.

Figure 7:
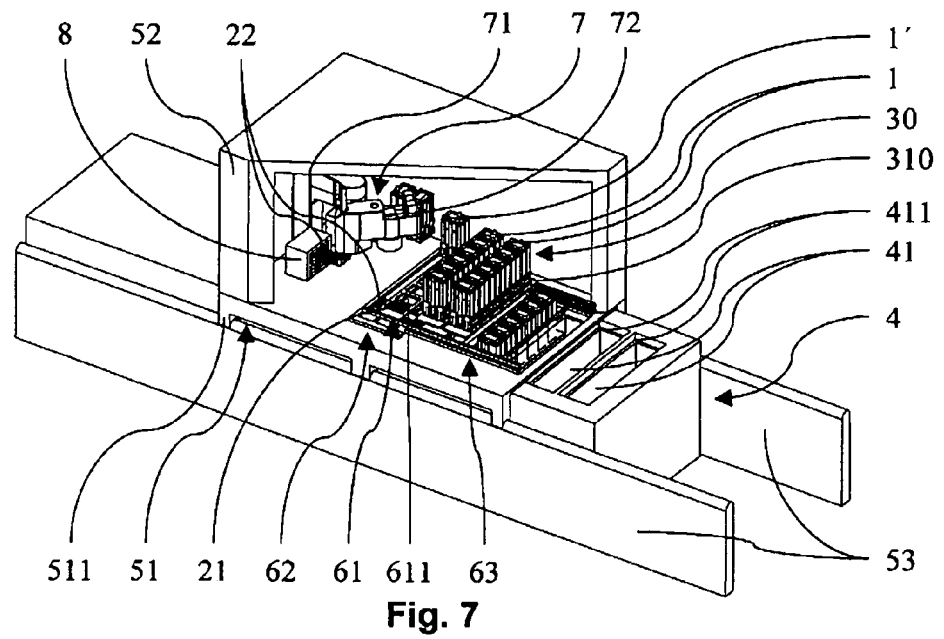
FIG. 7 shows a perspective view on microplate handling system according to the invention comprising a second embodiment of a storage unit according to the invention.

FIG. 7 shows a microplate handling system according to the invention comprising a freezer box 4 according to the invention in which a plurality of a second embodiment of storage units 30 according to the invention is arrangeable. The freezer box 4 has a cuboid shape and has a plurality of parallel shafts 41 with their open ends 411 arranged at a top side of the freezer box 4. Each of the storage units 30 has six stackers 1 arranged in a row as described above and a bottom plate 310 instead of the wider side plate 31 and the narrower side plate 32 of the first embodiment of a storage unit 3 (see FIG. 6) for fixing the six stackers 1 in its position relative to each other. Each of the shafts 41 is cooled, preferably to about −80° C., and arranged to accommodate one of the storage units 30. The storage units 30 can be dropped into and lifted out of a corresponding shaft 41 via the open end 411. For said lifting and dropping of the storage units 30 the microplate handling system comprises a gantry robot (not shown in FIG. 7).

Besides and along the freezer box 4 two parallel rails 53 are arranged on which a platform 51, i.e. a robotic platform, is movably positioned wherein the platform 51 has six feet 511 three of which being slidably arranged on one of the rails 53. The platform has three openings being arranged corresponding to the openings 411 of the freezer box 4. The gantry robot is arranged on top of the platform 51 such that it can lift a storage unit 30 out of one of the shafts 41 above the platform 51 via the open end 411 of the shaft 41 and via one of the openings of the platform 51. In FIG. 7 two storage units 30 are shown above the platform 51 and one of the storage units 30—the right hand one—is shown inside a corresponding shaft 41. The platform 51 can be moved along the rails 53 over the freezer box 4 such that each of the shafts 41 can be arranged underneath at least one of the openings of the platform 51.

Around the openings of the platform 51 a source microplate handling disposition 63 and at the left end of the source microplate handling disposition 63 a plate tray 61 and a delivery microplate handling disposition 62 as positioning disposition are arranged on the platform 51 wherein the plate tray 61 is arranged partly above the delivery microplate handling disposition 62. The plate tray 61 has six through-holes 611 corresponding to and in line with the six stackers 1 of the storage units 30. Exemplary, in FIG. 7 a source microplate 21 is arranged in one of the through-holes 611 of the plate tray 61.

On the left section of the platform 51 two interim storage racks 8 (in FIG. 7 only one interim storage rack 8 is visible) and a SCARA 7 are arranged. The SCARA 7 has a pedestal 71 being fixedly connected to the platform 51 and an arm 72 being movably connected to the pedestal 71. At the upper end region of the delivery microplate handling disposition 62 a single stacker 1' as described above for accommodating handled delivery microplates is arranged. Exemplary, in FIG. 7 one delivery microplate 22 is arranged on the delivery microplate handling disposition 62 as well as one delivery microplate 22 is arranged at the arm 72 of the SCARA 7. Further, a tempering cap 52 is arranged on the platform 51 covering the parts of the microplate handling system being arranged on the platform 51, comprising for example the SCARA 7, the interim storage racks 8, the delivery microplate handling disposition 62, the plate tray 61, the source microplate handling disposition 63, the delivery microplates 22, the gantry robot, and at least the lifted storage units 30. The tempering cap 52 is schematically shown diagonally opened for making its interior visible. Due to the tempering cap 52 it is possible to handle the source microplates 21 in the interior of the tempering cap 52 at a handling temperature, preferably about −20° C., which is not as cold as it is preferred for the long term storage of samples, particularly −80° C., but which is cold enough that the samples are not impaired during their handling, for example by thawing. At this handling temperature it is efficiently and economically possible that the mechanical movable parts of the microplate handling system, such as for example the SCARA 7, the delivery microplate handling disposition 62, the source microplate handling disposition 63, or the gantry robot, work properly.

Figure 8:
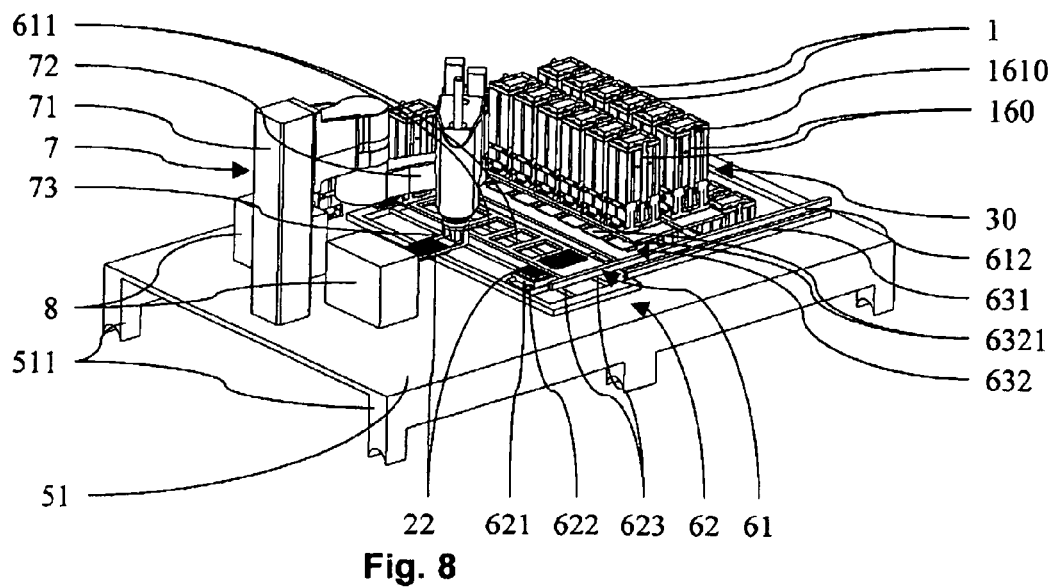
FIG. 8 shows a perspective view on selected parts of the microplate handling system from FIG. 7.
Figure 9:
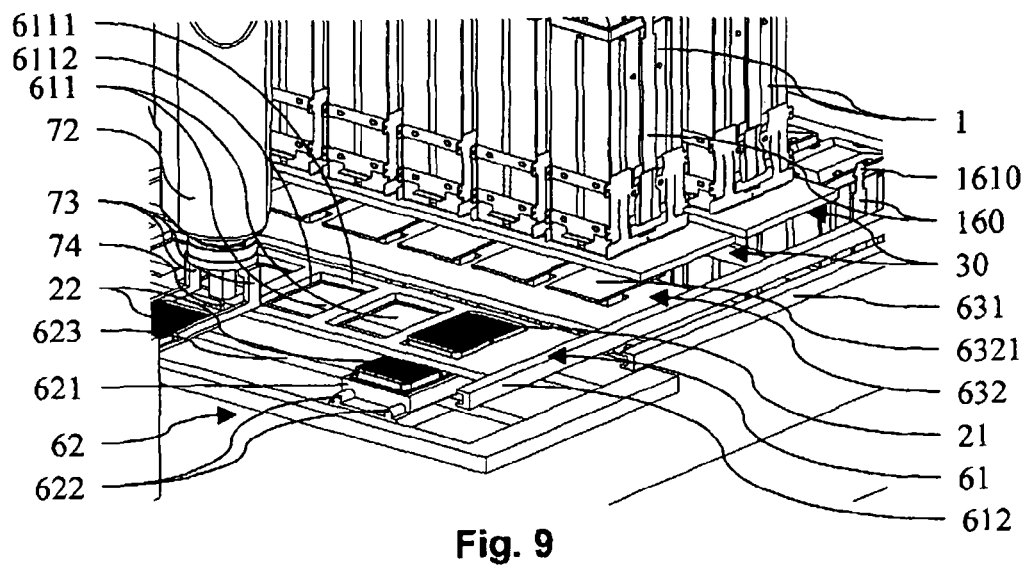
FIG. 9 shows another perspective view on selected parts of the microplate handling system from FIG. 7.

In FIG. 8 and in FIG. 9 parts of the microplate handling system are particularly shown for explaining the handling-movement of the source microplates 21 and of the delivery microplates 22. The delivery microplate handling disposition 62 comprises a sliding carriage 621 which is movably mounted on two parallel along rails 622 again being movably mounted on two parallel cross rails 623. The along rails 622 and the cross rails 623 are arranged perpendicularly and the sliding carriage 621 is movable under all of the six through-holes 611 of the plate tray 61. On the sliding carriage 621 a delivery microplate 22 is arranged which can be positioned under a source microplate 21 being arranged in any one of the through-holes 611 of the plate tray 61. The plate tray 61 is mounted at its longitudinal ends to two rails 612.

The SCARA 7 has gripping means 73 at the end of its arm 72 capable of clamping a delivery microplate 22 and transferring it from the sliding carriage 621 into one of the interim storage racks 8 and back. The source microplate handling disposition 63 which is arranged on a lower level than the plate tray 61 comprises removal means 632 being movably mounted at their longitudinal ends to two rails 631. The removal means 632 have six plate lifts 6321 each of them being arrangeable underneath one of the through-hole 611 of the plate tray 61 and underneath one of the stackers 1 of the lifted storage units 30. The storage units 30 have gripping means 160 with arrow heads 1610 allowing the gantry robot to grip a stacker and lifting it out of the freezer box 4 or dropping it into the freezer box 4, respectively.

In use one of the storage units 30 is lifted out of the freezer box 4 by the gantry robot and then a second storage unit 30 is arranged parallel and adjacent to the storage unit 30. For accommodating at least one microplate on the plate tray 61 the plate tray 61 is moved along the rails 612 until the six through-holes 611 lie exactly under the six removal gates 13 of the stackers 1. Simultaneously the removal means 632 are moved along the rails 631 until the six plate lifts 6321 lie exactly underneath the six through-holes 611. Then the at least one of the plate lifts 6321 is lifted through the corresponding through-hole 611 up to the corresponding stacker 1 and a source microplate 21 is released from the stacker 1 as described above. Said at least one plate lift 6321 is then dropped until the source microplate 21 is accommodated in the through-hole 611. For accommodating the source microplate 21 in the through-hole 611 of the plate tray 61 the border of the through-hole 611 has a step with a tread 6112 and a riser 6111 wherein the riser 6111 adjoins essentially perpendicularly to the top side of the plate tray 61 and the tread 6112 adjoins essentially perpendicularly to the riser 6111 such that the source microplate 21 is laid in the opening in a way that the tread 6112 contacts a border section of the bottom side of the source microplate 21 and that the riser 6111 fixes the source microplate 21. Then the plate tray 61 is moved back to a fixed microtube pushing position.

Figure 10:
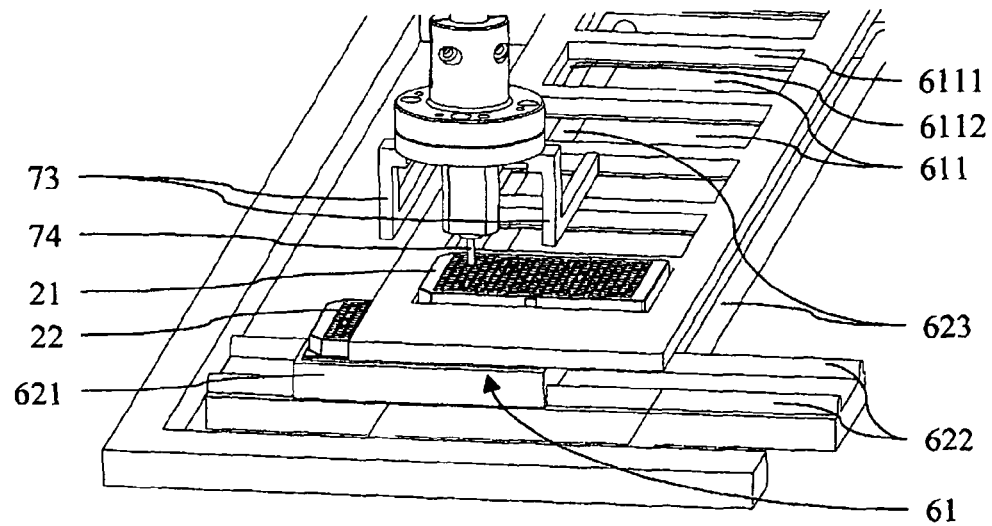
FIG. 10 shows a perspective view of selected parts of the microplate handling system from FIG. 7 particularly relevant for the pushing mechanism.

As best seen in FIG. 10 the SCARA 7 is equipped with a pin 74. For pushing predefined microtubes from the source microplate 21 being arranged on the plate tray 61 while it is in its microtube pushing position, the pin acts on each predefined microplate after another thereby relocating the microtube from the source microplate 21 into receiving means of the delivery microplate 22 arranged correspondingly under the microtube. For acting, the pin 74 can be disposable in relation to the arm 72 of the SCARA 7 by separate disposition means or it can be disposable by moving the arm 72 as a whole including the pin 74.

After the at least one source microplate 21 has been processed on the plate tray 61, the plate tray 61 and the plate lifts 6321 are positioned underneath the second storage unit 30 such that the at least one source microplate 21 can be relocated into one of the stackers 1 of the second storage unit 30 by the plate lift 6321 which is moved again through the corresponding opening of the plate tray 61. Then, the plate tray is ready to be loaded with the next at least one source microplate 21 from the storage unit 30. After all of the source microplates 21 of the storage unit 30 have been processed the source microplates 21 are arranged in the second storage unit 30 which can be dropped again into the freezer box 4 by the gantry robot.

When the delivery microplate 22 carries all predefined microtubes, for example selected by a client, it is relocated into the delivery stacker 1' such that the delivery stacker 1' has a plurality of delivery microplates 22 arranged in its interior, which for example can be delivery microplates 22 for several clients. For this relocation of the delivery microplate 22, the sliding carriage 621 is liftable upwardly. For being capable of parallel processing several delivery microplates 22 while processing one single storage unit 30, the delivery microplate 22 being arranged in the delivery microplate handling disposition 62 can be gripped by the gripping means 73 of the SCARA 7 such that the SCARA 7 can relocate the delivery microplate 22 in the interim storage rack 8.

Figure 11:
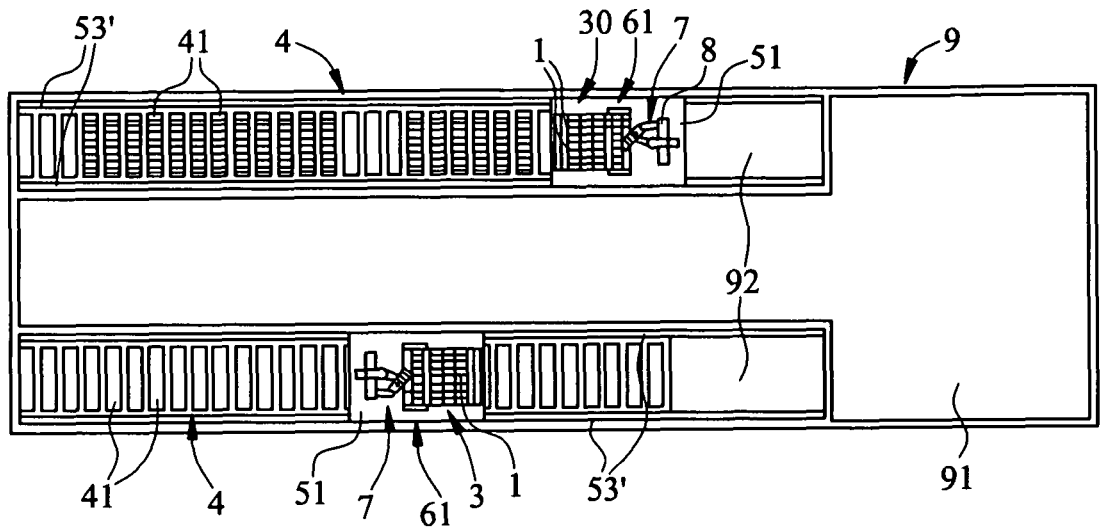
FIG. 11 shows a top view on a cold room according to the invention.
Figure 12:
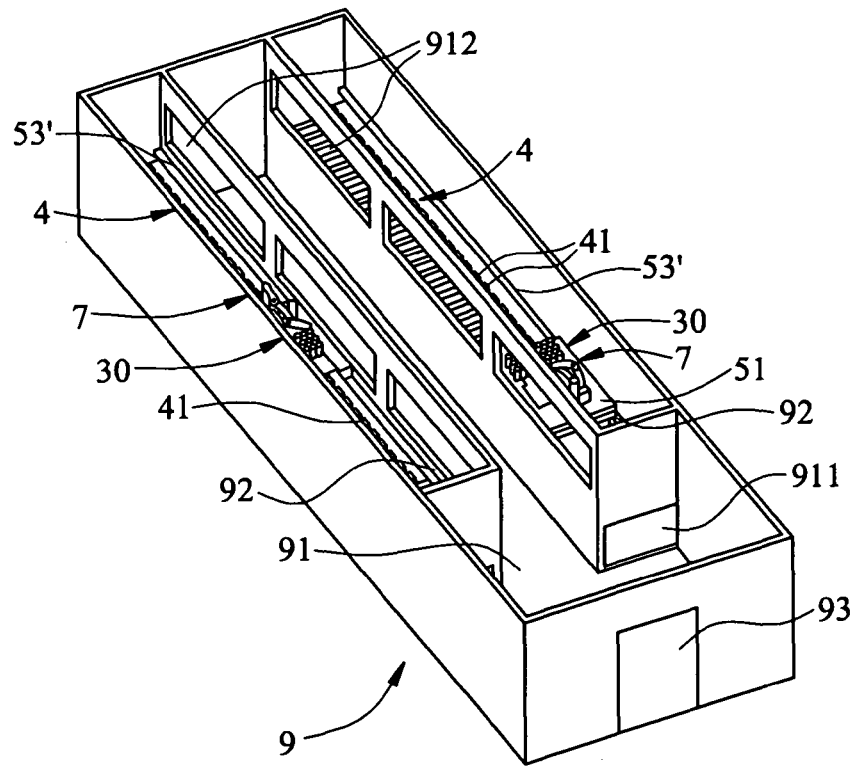
FIG. 12 shows a perspective view of the cold room from FIG. 11.

FIG. 11 and FIG. 12 show an embodiment of a cold room 9 according to the invention. The cold room 9 comprises a first compartment 91, second compartments and two third compartments 92. The second compartments consist of a plurality of shafts 41 of freezer boxes 4 being arranged inside the third compartment 92. Above each of the freezer boxes 4 a platform 51 carrying a SCARA 7 is movable on rails 53'. The first compartment 91 is connected to each of the third compartments 92 by a docking port 911. The first compartment 91 is human accessible via a door 93. Further, the third compartments 92 have windows through which the inside of the third compartments 92 is visible from the first compartment 91.

In use, the first compartment 91 is preferably cooled to a temperature of about +4° C. such that human beings can comparably conveniently work inside the first compartment 91. The third compartments 92 are thereby preferably cooled to about −20° C. such that the automated mechanical handling of microplates by the SCARA 7 is economically possible. Further, the second compartments, i.e. the shafts 41 of the freezer boxes 4 are preferably cooled to about −80° C. or less such that long term storage of samples is possible. The freezer boxes 4 are conveniently accessible via the docking ports 911. The dry-air conditioning system of the cold room 9 prevents frost built-up during microplate storage and during microplate handling.

Figure 13:
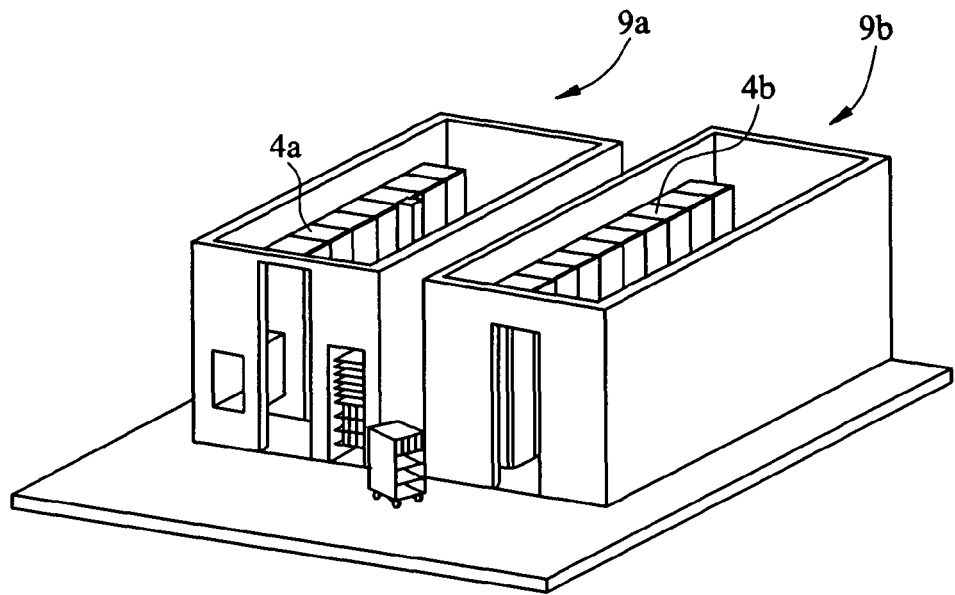
FIG. 13 shows a perspective view of an arrangement of further embodiments of cold rooms according the invention.
Figure 14:
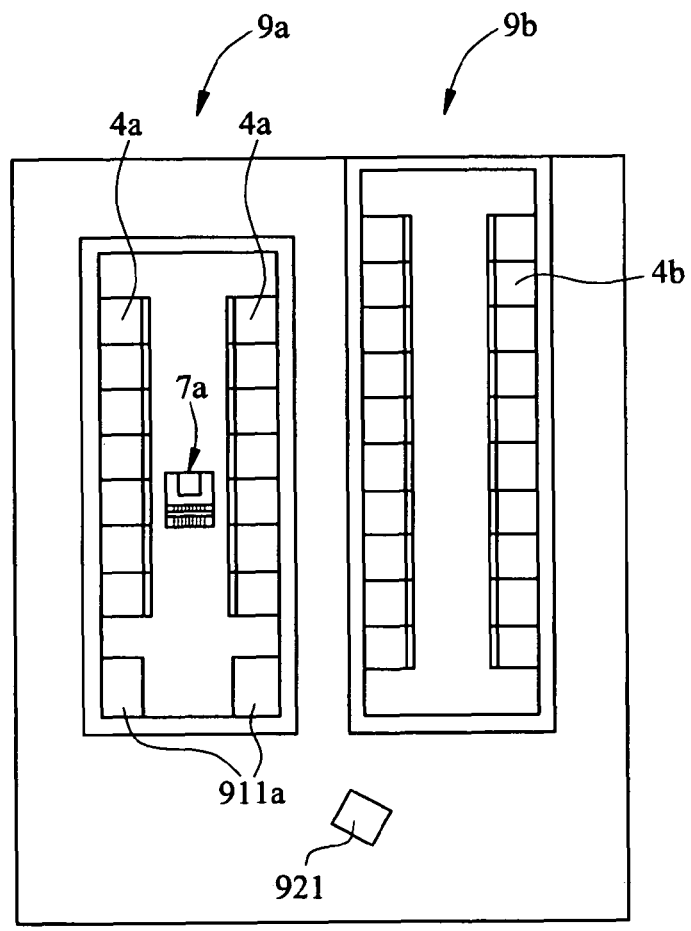
FIG. 14 shows a top view of the arrangement of cold rooms of FIG. 13.

FIG. 13 and FIG. 14 show an arrangement of further embodiments 9a and 9b of cold rooms. Cold room 9a is embodied as a "robotic store" in which a plurality of upright standing −80° C. freezer boxes 4a are arranged, in which stackers 1 or storage units 3 can be stored. A robot 7a for handling of stackers 1, or storage units 3, or microplates with microtubes is arranged to be movable along the corridor formed between the two rows of freezer boxes 4a. The temperature in the space where robot 7a is arranged is about −20° C. Input and output buffers 911a can be provided as an interface allowing a human operator to take stackers or storage units out from the robotic store or to put them into the robotic store manually or with the aid of robot 7a. The stackers or storage units taken out from the robotic store can be put into a mobile transport freezer box 921 which can be docked at the input/output buffers 911a so as to maintain the cold-chain. The same holds for the transfer of a stacker or storage unit from the mobile transport freezer box into the robotic store. Such a "robotic store" is particularly suitable for the storage of samples which are used during clinical studies where many of the samples have to be accessed from time to time during the duration of the clinical studies.

Cold room 9b, on the other hand, is embodied as an "archive store" and comprises a plurality of upright standing −80° C. freezer boxes 4b. However, cold room 9b does not comprise a robot, since usually the samples stored in the −80° C. freezer boxes 4b need not be accessed or need only be accessed in extremely rare cases. Nevertheless, even after a clinical study has been finished there may be an obligation or the desire to further store the samples for a certain time period (e.g. for up to fifteen years), normally without the need to access the samples stored in the archive store, but with the possibility to analyze a sample at a later date. To store said "archive" samples also in a "robotic store" would require a larger "robotic store" and this would represent an expense that is too high for the intended purpose. In case a sample is needed from a −80° C. freezer box 4b, an operator is to take them out from the respective freezer box 4b on an individual basis with the aid of suitable means, however, it has to be borne in mind that this only happens in rare cases. Using the modules "robotic store" and "archive store" it is easy to scale up the storage facilities in accordance with the specific needs, that is to say depending on whether storage facilities for samples for clinical studies or whether long term storage facilities for samples that need usually not be accessed are needed.

Figure 15:
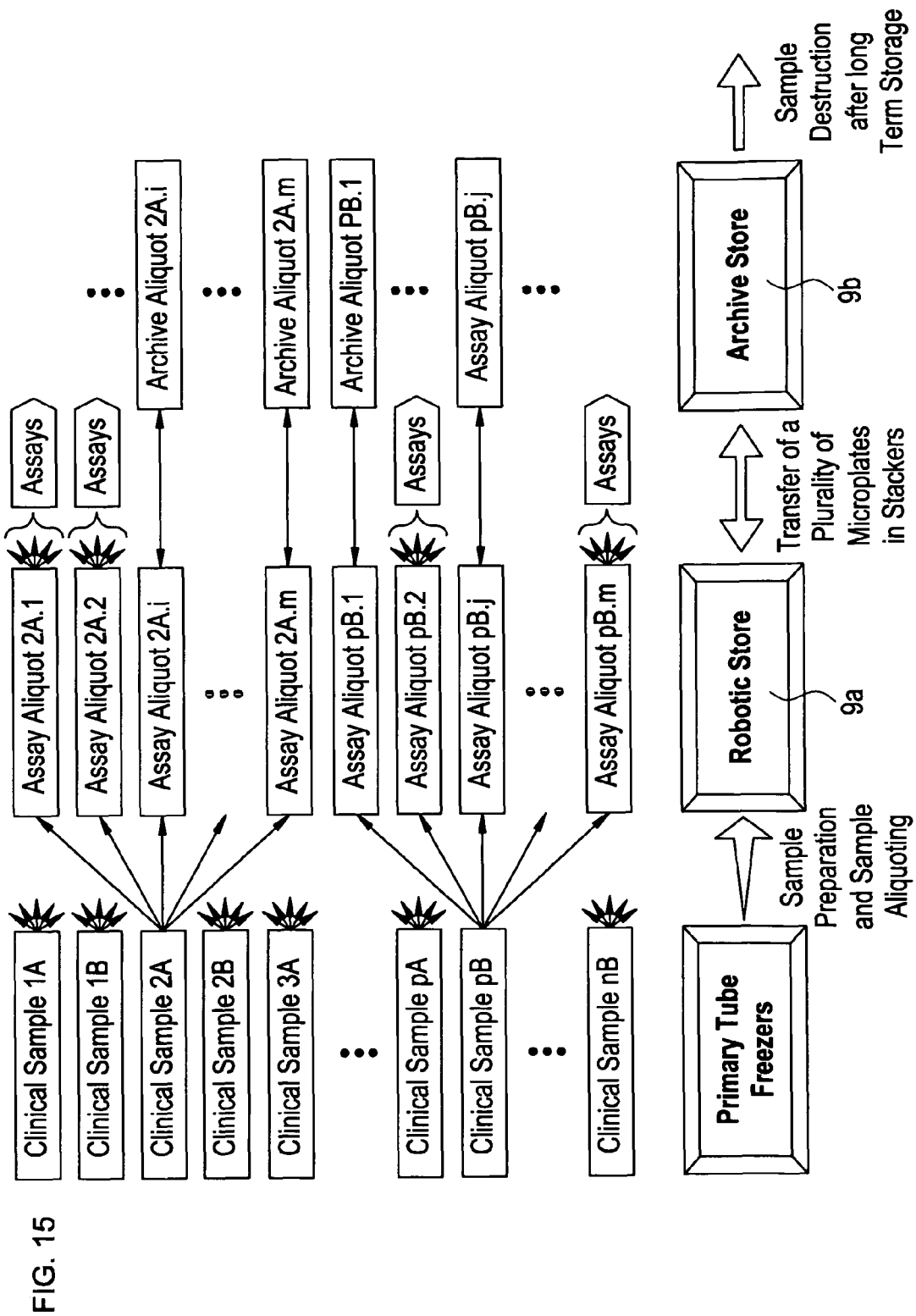
FIG. 15 shows an embodiment of a sample flow during and after a clinical study.

FIG. 15 shows an embodiment of a sample flow during and after a clinical study. For that reason, clinical samples (A- and B-samples) 1A,1B,2A,2B . . . , pB, . . . nB are first stored in so-called primary tube freezers where they are gathered and temporarily stored. The samples are then prepared for several assays and split up into multiple aliquots for a multitude of assays. For example, clinical sample 2A is prepared and split up into multiple aliquots 2A.1,2A.2,2A.i, . . . 2A.m. Of course, the aliquots prepared for the assays can be split up into further aliquots for sub-assays. The aliquots are then transferred to a robotic store, such as robotic store 9a shown in FIG. 13 and FIG. 14. During a clinical study, the aliquots stored in robotic store 9a can be accessed comparatively easily, as has been described in detail above. Those aliquots which are not needed for the clinical study can be transferred to an archive store, such as archive store 9b shown in FIG. 13 and FIG. 14. If desired or if necessary, the aliquots stored in archive store 9b can be transferred back to the robotic store 9a, or they can be destroyed when they are no longer needed.

The invention claimed is:

1. A stacker adapted for storing a plurality of microplates in an about −80° C. environment, the stacker comprising a housing and a gate for loading a microplate into and removing a microplate from the housing, respectively, the microplates each having a top surface side and a bottom surface side opposed to the top surface side, the stacker being adapted to accommodate the plurality of microplates inside the housing in a stack such that adjacent microplates abut with their top and bottom surfaces, respectively, wherein the housing comprises four essentially perpendicularly arranged side walls completely surrounding the interior of the housing, a top longitudinal end closed by a cover and an open bottom longitudinal end where the gate is arranged, each of the side walls having a contoured section slightly extending into the interior of the housing for adjoining each microplate accommodated in the housing, and wherein the gate has holding means for holding the plurality of microplates inside the housing and for releasing them from the housing, the holding means including two angled, flat spring like sheets each having a mounting portion attached to one of two opposing side walls and a retention portion forming an acute angle with the mounting portion, said spring like sheets being mounted with their mounting portions to two opposing side walls of the housing, whereby in a closed state of the stacker said retention portions protrude over a border of said bottom longitudinal end into the interior of said housing and provide a rest for the microplates accommodated in the housing, said mounting portions being resiliently bendable partly away from the side walls such that the retention portions are moved sidewardly clear of said bottom longitudinal end of the housing thereby bringing the stacker into an open state in which a microplate can be discharged out of or loaded into the housing via said bottom longitudinal end, the mounting portions of the spring like sheets being relaxed when the stacker is in its closed state and being tensioned when the stacker is in its open state.

2. A storage unit comprising a plurality of fixedly interconnected stackers according to claim 1, wherein each of the stackers adjoins to its adjacent stacker.

3. The storage unit of claim 2, wherein the stackers are arranged in a row.

4. The storage unit of claim 2 further comprising a bottom plate being connected to a bottom end of each of the stackers.

5. The storage unit of claim 4, wherein the bottom plate comprises removal openings for removing microplates out of the storage unit, each being arranged adjacent to the removal gate of one of the stackers.

6. The storage unit of claim 2 further comprising lifting means.

7. A freezer box for tempering
(a) a stacker according to claim 1; or
(b) a storage unit, comprising a plurality of fixedly interconnected stackers according to (a), wherein each of the stackers adjoins to its adjacent stacker;
wherein the freezer box comprises a temperable interior which is arranged for accommodating the stacker of (a) or the storage unit of (b), and further comprising an opening at a top side or front side for receiving and removing the stacker of (a) or the storage unit of (b) into and out of the interior of the freezer box.

8. The freezer box of claim 7, further comprising a cuboid shape and a plurality of shafts, wherein each shaft has its open end at the top side of the freezer box and each shaft is arranged for accommodating a stacker or a storage unit.

9. A microplate handling system comprising a freezer box according to claim 7, a plate tray, a positioning disposition and a robot arm, wherein the plate tray and the positioning disposition are arranged to accommodate at least one source microplate with a plurality of microtubes and a delivery microplate such that a top surface side of the delivery microplate is arrangeable facing a bottom surface side of the at least one source microplate, wherein the positioning disposition has moving means for moving the at least one source microplate and the delivery microplate parallel in relation to each other into a predefined position when the plate tray and the positioning disposition accommodate the at least one source microplate and the delivery microplate, and wherein the robot arm has pushing means for pushing a predefined microtube of the plurality of microtubes from the at least one source microplate into the delivery microplate when the plate tray and the positioning disposition accommodate the at least one source microplate and the delivery microplate and when the at least one source microplate and the delivery microplate are moved to the predefined position by the moving means.

10. The microplate handling system of claim 9, wherein the plate tray is arranged for fixedly accommodating the at least one source microplate in a predefined position and the positioning disposition is arranged for movably accommodating the delivery microplate, wherein the moving means of the positioning disposition are arranged for moving the delivery microplate with its top surface side parallel to the bottom surface side of the at least one source microplate into the predefined position when the positioning disposition accommodates the delivery microplate and the plate tray accommodates the at least one source microplate.

11. The microplate handling system of claim 10, wherein the plate tray has at least one through-hole adjoining the bottom surface side of the at least one source microplate when the plate tray accommodates the at least one source microplate.

12. The microplate handling system of claim 10 further comprising a source microplate handling disposition having removal means for removing the at least one source microplate out of a first stacker or out of a first storage unit when the first stacker or the first storage unit is lifted out of the freezer box, accommodation means for transferring the at least one source microplate to the plate tray and for accommodating the at least one source microplate on the plate tray, as well as putting means for transferring the at least one source microplate from the plate tray to a second stacker or a second storage unit and for putting the at least one source microplate into the second stacker or the second storage unit.

13. The microplate handling system of claim 9 further comprising a platform being arranged on top of the freezer box, and a gantry robot being arranged on the platform, wherein the platform has a through hole and the gantry robot has gripping means for gripping the stacker or the storage unit such that the stacker or the storage unit is liftable through the through hole of the platform out of the freezer box by the gantry robot and such that the stacker or the storage unit is dropable through the through hole of the platform into the freezer box by the gantry robot.

14. The microplate handling system of claim 13 further comprising a tempering cap being tightly connected to the platform, having tempering means and enclosing the plate tray, the positioning disposition, the robot arm, and the gantry robot, such that the interior of the tempering cap is temperable by the tempering means separately from the tempering of the freezer box.

15. The microplate handling system of claim 9 further comprising a delivery microplate handling disposition having an additional stacker and putting means for transferring the delivery microplate to the additional stacker and for putting the delivery microplate into the additional stacker.

16. The microplate handling system of claim 9 further comprising an interim storage, wherein the robot arm has gripping means for gripping the delivery microplate, such that the delivery microplate is moveable into the interim storage by the robot arm.

17. A cold room for a microplate handling system according to claim 9 comprising at least a first compartment, a second compartment, a third compartment and a dry-air conditioning system, wherein the first compartment being operated at an elevated temperature has a docking port for loading the freezer box of the microplate handling system into the cold room and for de-loading the freezer box of the microplate handling system out of the cold room, wherein the second compartment is operated at a low temperature for storing a stacker according to or a storage unit according to, and wherein the third compartment is operated at an intermediate temperature for automated microplate handling.

18. A microplate handling method using the microplate handling system of claim 9 comprising the steps of:
(a) tempering the freezer box to a predefined temperature range;
(b) storing a plurality of storage units with a plurality of stackers each having a plurality of source microplates with a plurality of microtubes inside the freezer box;
(c) providing an empty second storage unit corresponding to the storage unit;
(d) accomodating a delivery microplate on the positioning disposition;
(e) moving one storage unit of the plurality of storage units out of the freezer box;
(f) transferring at least one source microplate via the removal gate of the corresponding at least one stacker to the plate tray;
(g) simultaneously positioning the delivery microplate and the robot arm such that a bottom side of a predefined microtube of the at least one source microplate is arranged adjacent to a top surface side of the delivery microplate at predefined receiving means of the delivery microplate and such that the pushing means of the robot arm are arranged adjacent to a top side of the predefined microtube;

(h) pushing the predefined microtube from the at least one source microplate into the predefined receiving means of the delivery microplate by means of the robot arm;
(i) repeating steps (g) and (h) until all predefined microtubes of the at least one source microplate are pushed into the delivery microplate;
(j) transferring the at least one source microplate into the second storage unit;
(k) repeating steps (f) through (j) until all source microplates of the storage unit are located inside the second storage unit; and
(l) moving the second storage unit into the freezer box.

* * * * *